Figure 1:
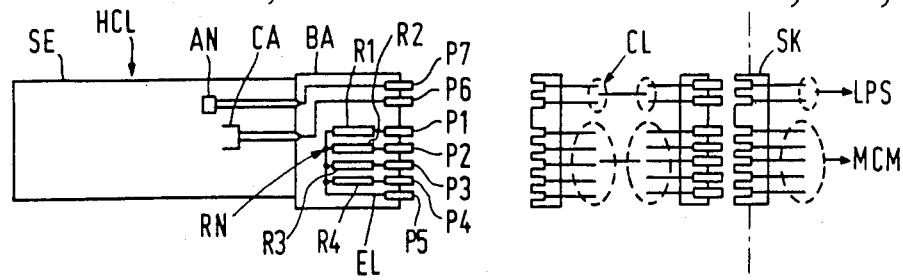

United States Patent [19]

Stockdale

[11] Patent Number: 4,634,277
[45] Date of Patent: Jan. 6, 1987

[54] ATOMIC ABSORPTION SPECTROPHOTOMETER AND METHOD OF ANALYSIS BY ATOMIC ABSORPTION SPECTROPHOTOMETRY

[75] Inventor: Trevor J. Stockdale, Cambridge, England

[73] Assignee: U.S. Philips Corporation, New York, N.Y.

[21] Appl. No.: 750,664

[22] Filed: Jun. 1, 1985

Related U.S. Application Data

[63] Continuation of Ser. No. 456,238, Jan. 7, 1983, abandoned.

[30] Foreign Application Priority Data

Jan. 19, 1982 [GB] United Kingdom ............... 8201373

[51] Int. Cl.$^4$ .......................................... G01N 21/72
[52] U.S. Cl. ....................................................... 356/315
[58] Field of Search ............... 356/311, 315, 316, 317, 356/318, 319; 364/497, 498, 526

[56] References Cited

U.S. PATENT DOCUMENTS

| 4,176,957 | 12/1979 | Magda et al. | 356/319 |
| 4,234,252 | 11/1980 | Bötteer et al. | 356/315 |
| 4,314,764 | 2/1982 | Liddell et al. | 356/315 |
| 4,322,807 | 3/1982 | Chamran et al. | 356/319 |
| 4,330,207 | 5/1982 | Nogami et al. | 356/318 |
| 4,449,820 | 5/1984 | Koizumi et al. | 356/315 |

OTHER PUBLICATIONS

C. Falinower, "Automatic Analysis by Atomic Absorption Spectrophotometry", *Atomic Absorption Newsletter*, vol. 14, No. 6, 12-1975, pp. 145-148.
M. J. Fishman et al., "Automation of Atomic Absorption Analysis", *Atomic Absorption Newsletter*, vol. 9, No. 4, 8-1970, pp. 88-89.
C. K. Deak, "Internal Standard Method for Rapid Identification of Materials by Atomic Absorption Spectrophotometry", *Atomic Absorption Newsletter*, vol. 10, No. 1, 2-1971, pp. 6-8.
The Perkin-Elmer Model 4A Series Automated Atomic Absorption Analyzers, 11-1968.
Morgenthaler et al., "A Microcomputer System for Control of an Atomic Absorption Spectrometer", *American Laboratory*, vol. 8, No. 8, 8-1976, pp. 37-45.

*Primary Examiner*—Davis L. Willis
*Assistant Examiner*—S. A. Turner
*Attorney, Agent, or Firm*—Paul R. Miller

[57] ABSTRACT

A method of analyzing using an atomic absorption spectrophotometer including a flame atomizer is disclosed. The method comprises the steps of (a) setting the parameters of the spectrophotometer to a set of preset values dependent on the substance to be detected, (b) setting the gas flow rate to the burner to a preset value dependent on the substance to be detected, (c) aspirating an optimization standard into the flame, (d) measuring the absorbance of the optimization standard and storing the result, (e) modifying the gas flow rate in incremental steps and at each incremental step of flow rate repeating steps (c) and (d), and comparing the new absorbance value with the stored value until a maximum absorbance measurement is found, (f) using the maximum absorbance measurement value to select one of a plurality of sets of parameters for the spectrophotometer, and (g) subsequently aspirating and measuring the absorbance of a sample using the selected set of parameters. A first set of parameters is selected if the absorbance value is less than 0.1 absorbance units, the original set of parameters is retained if the absorbance value is between 0.1 and 0.5 absorbance units, and a third set of parameters is selected if the absorbance value is greater than 0.5 absorbance units. An atomic absorbance spectrophotometer in which this method is automatically carried out under the control of a microcomputer is also set forth.

23 Claims, 7 Drawing Figures

ATOMIC ABSORPTION SPECTROPHOTOMETER AND METHOD OF ANALYSIS BY ATOMIC ABSORPTION SPECTROPHOTOMETRY

This application is a continuation of application Ser. No. 456,238, filed Jan. 7, 1983, and the benefits for such previous application are hereby claimed for this new continuation application now abandoned.

The invention relates to an atomic absorption spectrophotometer and to a method of analysis by atomic absorption spectrophotometry.

When analysing a substance using an atomic absorption spectrophotometer including a flame atomizer it has been necessary for the operator to optimize the setting of a number of parameters. These parameters are the operating current of the radiation sources, commonly hollow cathode lamps, and hence the intensity of the radiation, the flow rate of the fuel gas to the burner, the bandpass characteristics of the monochromator, by adjusting the width of the entrance and exit slits, and the measurement time. This optimization of the parameters is time consuming and puts considerable demands on the skill of the operator.

It is an object of the invention to provide an atomic absorption spectrophotometer in which it is unnecessary for the operator to optimize the parameters.

The invention provides an atomic absorption spectrophotometer comprising a flame atomizer; means for setting parameters of the spectrophotometer to a first set of preset values dependent on the substance to be detected; means for setting the fuel gas flow rate to the burner to a preset value dependent on the substance to be detected; means for aspirating an optimization standard sample into the flame; means for measuring the absorbance of the optimization standard and means for selecting one of a plurality of stored sets of parameters of the spectrophotometer dependent on the absorbance of the optimization standard.

An atomic absorption spectrophotometer according to the invention has the advantage that when an indication of the substance to be detected has been entered into the instrument it is capable of setting itself up to its optimum conditions without the aid of the operator. If as in the embodiment described coded lamps are fitted the indication of the substance to be detected may be read by a microprocessor in the instrument which then retrieves appropriate sets of parameters from a non-volatile memory.

When a substance to be detected has a sensitivity which varies with the rate of fuel gas flow to the burner the spectrophotometer may comprise means for measuring the absorbance of the optimization standard and for storing the result; means for modifying the gas flow rate to the burner in incremental steps, for measuring the absorbance of the optimisation standard at each step, and for cmparing the measured absorbance at each step with that measured at the preceding step to determine the flow rate giving the maximum absorbance; and means for selecting one of a plurality of stored sets of parameters of the spectrophotometer dependent on the maximum absorbance value.

The spectrophotometer may be arranged so that the first set of parameters is retained if the maximum absorbance value or the absorbance of the optimization standard is in the range 0.1 to 0.5 Absorbance Units, a second set of parameters is used if the maximum absorbance value or the absorbance of the optimization standard is less than 0.1 Absorbance Units, and a third set of parameters is used if the maximum absorbance value or the absorbance of the optimization standard is greater than 0.5 Absorbance Units.

Means may be provided for selecting radiation of an alternative wavelength if the maximum absorbance value or the absorbance of the optimization standard is greater than 1.0 Absorbance Units.

This may enable a lower absorbance value to be obtained thus reducing the effect of noise.

Means may be provided for indicating whether the maximum absorbance value or the absorbance of the optimization standard is greater than 0.5 Absorbance Units. This enables the operator to be alerted to possible inaccuracies in the measured concentrations.

Means may be provided for diluting the optimization standard, with the diluting means being activated when the maximum absorbance value or the absorbance of the optimization sample is greater than 0.5 Absorbance Units and being effective to bring the maximum absorbance value or absorbance of the diluted optimization standard within the range 0.1 to 0.5 Absorbance Units. This enables the measurements to be made in the most sensitive part of the range of the instrument. The sample to be measured is, of course, also appropriately diluted.

The invention further provides a method of analysis using an atomic absorption spectrophotometer including a flame atomizer comprising the steps of (a) setting the parameters of the spectrophotometer to a set of preset values dependent on the substance to be detected, (b) setting the gas flow rate to the burner to a preset value dependent on the substance to be detected, (c) aspirating an optimization standard into the flame, (d) measuring the absorbance of the optimization standard and storing the result, (e) modifying the gas flow rate in incremental steps and at each incremental step of flow rate repeating steps (c) and (d) and comparing the new absorbance value with the stored value until a maximum absorbance measurement is found, (f) using the maximum absorbance measurement value to select one of a plurality of sets of parameters for the spectrophotometer, and (g) subsequently aspirating and measuring the absorbance of a sample using the selected set of parameters.

Figure 2:
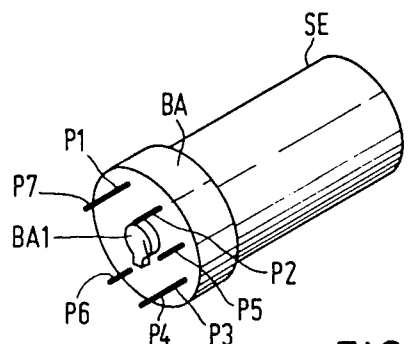
Figure 3:
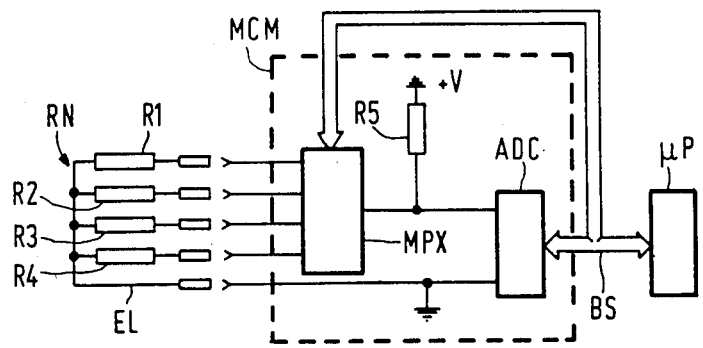
Figure 4:
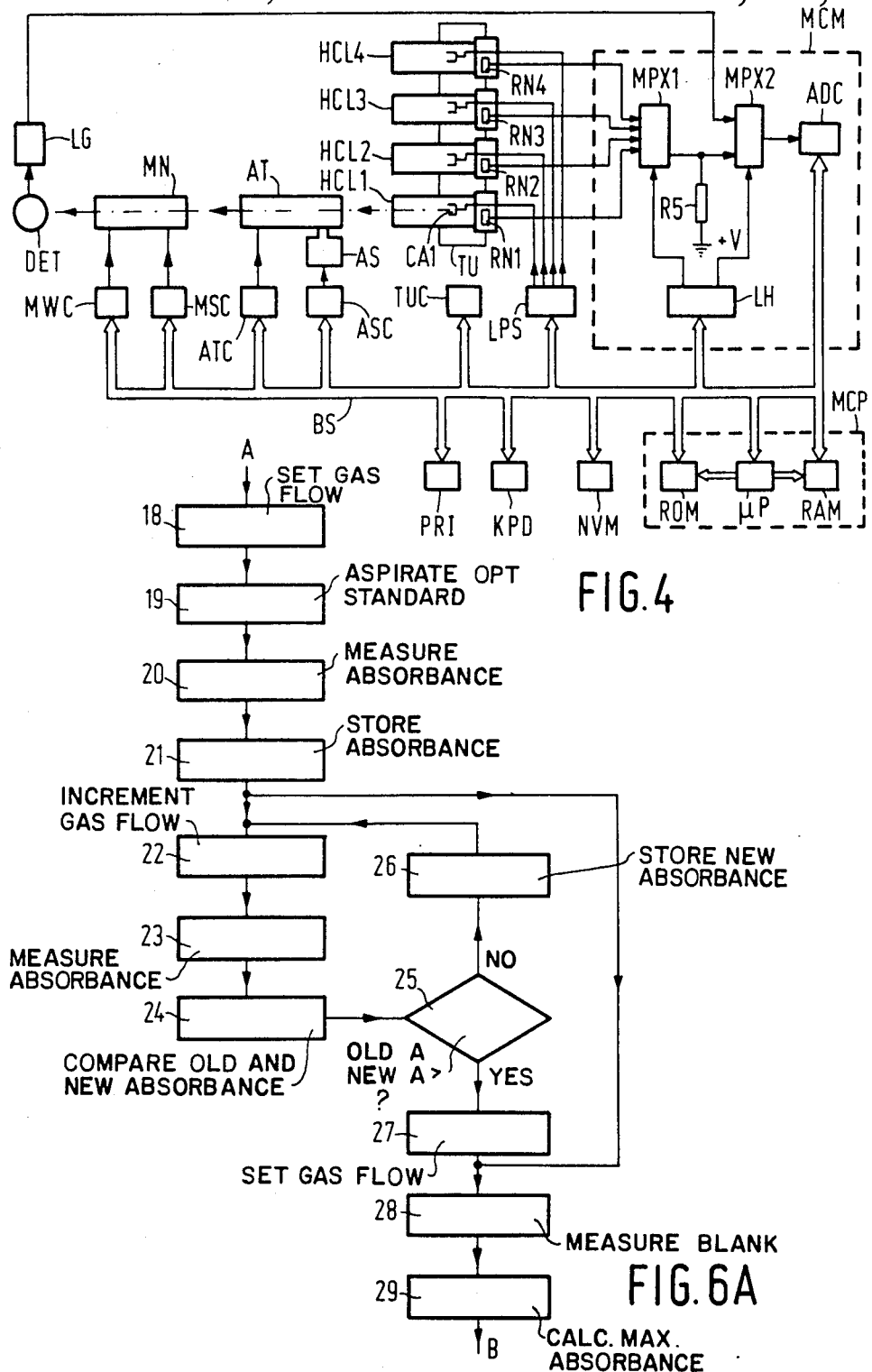
Figure 5:
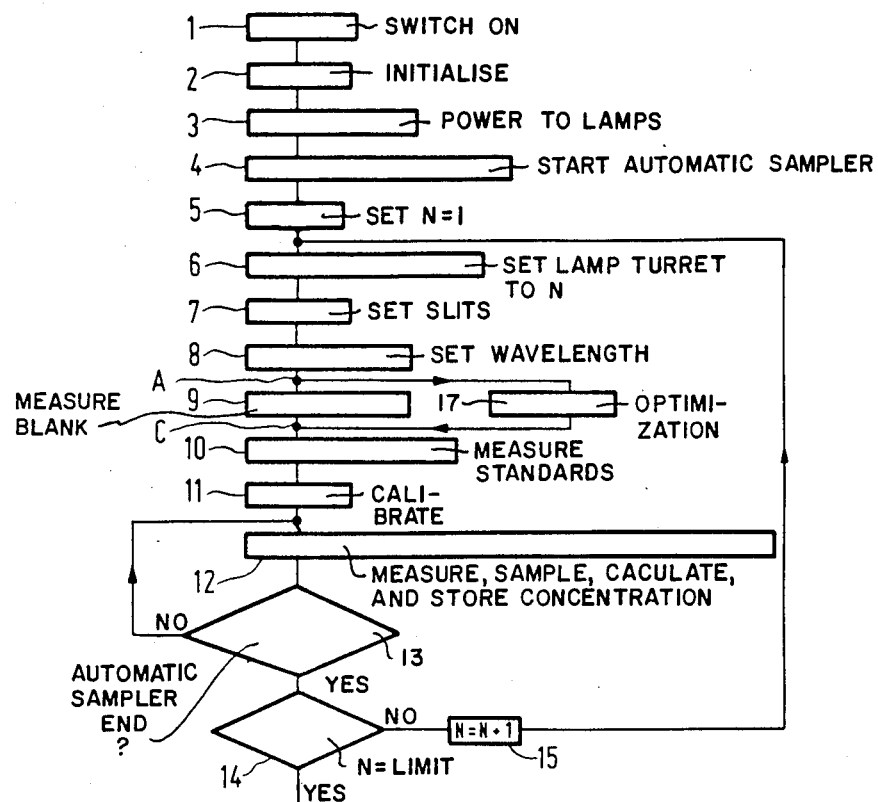
Figure 6B:
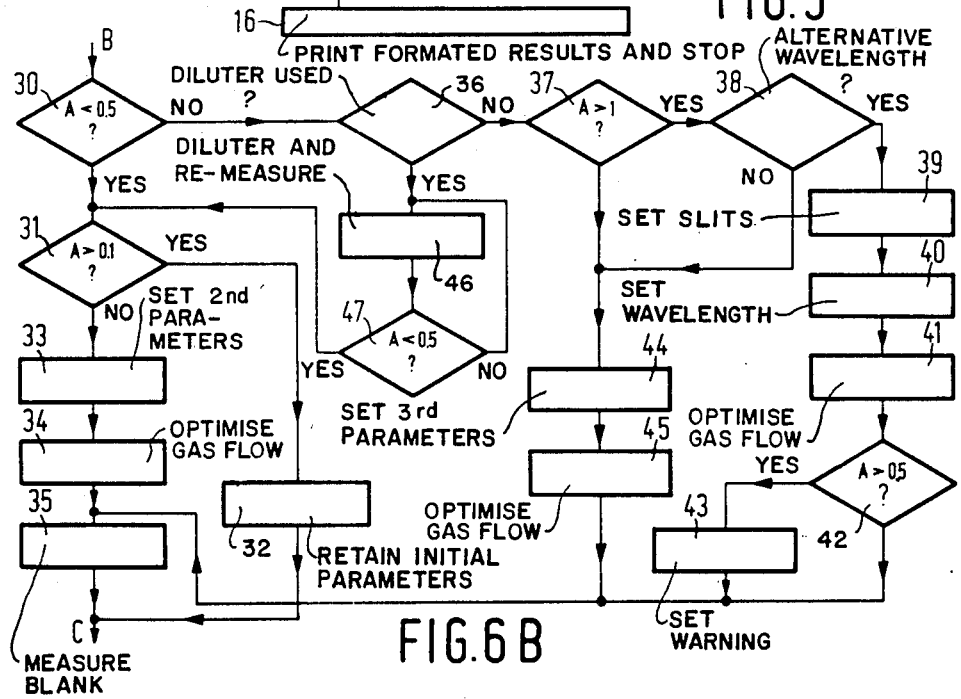

An embodiment of the invention will now be described, by way of example, with reference to the accompanying drawings in which:

FIG. 1 shows a schematic section view of a single atomic element hollow cathode lamp assembly and electrical connectors directly associated therewith, FIG. 2 shows a perspective view of the lamp assembly of FIG. 1, FIG. 3 shows the resistor network of the lamp assembly of FIG. 1 and measurement circuit means of a spectrophotometer using that lamp, FIG. 4 shows an atomic absorption spectrophotometer using four lamp assemblies as in FIG. 1, FIG. 5 is a flow chart of an operation of the spectrophotometer shown in FIG. 4, and FIGS. 6A and 6B are flow chart representations of a sub-routine for a spectrophotometer according to the invention which is inserted between points A and C in the flow chart of FIG. 5.

Referring now to FIGS. 1 and 2, a single atomic element hollow cathode lamp assembly HCL has a lamp formed by a hollow cathode electrode CA and an anode electrode AN within a sealed envelope SE. A base BA is attached to the envelope SE, and located within the base BA is a resistor network RN consisting of four resistors R1, R2, R3 and R4 connected to a common lead EL. Two plug terminals P6 and P7 protruding from the base BA and connected respectively to the electrodes CA and AN provide connecting means for connecting these electrodes to lamp power supply means LPS (see FIG. 4). Five plug terminals P1 to P5 protruding from the base BA and connected respectively to the resistors R1 to R4 and the lead EL provide further connecting means for including the resistor network in measurement circuit means MCM (see FIGS. 3 and 4) in an atomic absorption spectrophotometer. The resistor network is representative of the atomic element of the lamp by virtue of the resistors R1 and R2 and is furthermore representative of a lamp operating current by virtue of the resistors R3 and R4. As shown in FIG. 2, the terminals P1 to P7 are arranged in a conventional octal plug configuration with a boss BA1 on the base BA for ensuring correct electrical connection.

When in the operative position in a spectrophotometer, the lamp assembly HCL will be located in the optical path thereof and electrical connection from the terminals P1 to P7 to a fixed socket SK in the spectrophotometer will be made via a connecting lead CL with socket and plug connectors. Instead of being located within the base BA the resistor network RN could possibly be located within the connecting lead CL, and in this case the lead CL can be considered as forming part of the lamp assembly with appropriate parts of the lead CL providing part of the connecting means for the electrodes and providing the whole of the said further connecting means for the network. Another possibility would be to locate the network RN inside the sealed envelope SE. Both these possible variations from the arrangement shown in FIGS. 1 and 2 indicate that it is not necessary for the lamp to be provided with a separately identifiable base.

Referring now to FIG. 3, the resistor network RN is shown together with measurement circuit means MCM and a microprocessor μP in a spectrophotometer. The measurement circuit means MCM includes a multiplexer MPX and an analogue-to-digital converter ADC respectively controlled by and connected to the microprocessor μP via a bus BS, and a resistor R5 connected to a voltage source +V. By means of the multiplexer MPX the resistors R1 to R4 are connected in turn in series with the resistor R5 and the common lead EL and hence the voltage across each of the resistors R1 to R4 in turn is applied to the analogue-to-digital converter ADC. The ohmic values of the two resistors R1 and R2 together represent the atomic element of the single atomic element hollow cathode lamp assembly incorporating the network; conveniently one of these two resistors represents the tens value and the other resistor represents the units value of the atomic number of the atomic element. The ohmic values of the two resistors R3 and R4 together represent a lamp operating current; conveniently the maximum operating current for the electrodes of the lamp assembly incorporating the network. The microprocessor μP is conditioned to identify the atomic element responsive to measurement of the resistor network by the measurement circuit means MCM, that is to say the two successive digital outputs of the converter ADC responsive to the resistors R1 and R2. The lamp current information derived by the measurement circuit means MCM from the resistor network, that is to say the two successive digital outputs of the converter ADC responsive to the resistors R3 and R4, is used by the microprocessor μP together with other lamp current information, as will be described in detail with reference to FIGS. 4 and 5, to control the lamp power supply means LPS connected to the electrodes of the respective hollow cathode lamp.

It will be appreciated that although the resistive network as described is inexpensive and convenient the electrical network incorporated in the hollow cathode lamp assembly as described above to represent the atomic element and the maximum lamp operating current could be other than resistive. With suitably adapted measurement circuit means, the network could for example be capacitive or it could provide a binary representation by using connections which are open or short circuit or by using diodes.

The single atomic element hollow cathode lamp provided with an electrical network as described above with reference to FIGS. 1 and 2 is one example of a source lamp assembly for an atomic absorption spectrophotometer. Other lamps for producing resonance line radiation characteristics of one or more atomic elements when operated by lamp power supply means may be provided with similar networks to form atomic absorption spectrophotometer source lamp assemblies. One such other lamp is an electrodeless discharge lamp. In this case an electrical network may be similarly provided in an assembly with the lamp to enable the single atomic element for which the lamp emits resonance line radiation to be identified in the spectrophotometer. Electrodeless discharge lamps are usually provided with an auxiliary power supply external to the spectrophotometer. The network in the lamp assembly in this case could also represent a particular value of electrical power which is identified in the spectrophotometer and used to control the auxiliary power supply. Another such other lamp is a multiple atomic element hollow cathode lamp. In this case also an electrical network may be provided in an assembly with the lamp to enable all the atomic elements for which the lamp emits resonance line radiation to be identified in the spectrophotometer. Multiple atomic element hollow cathode lamps conventionally emit resonance line radiation for particular combinations of two, three or four atomic elements, and the network could represent these atomic elements individually or it could represent the particular combination. The network could also represent a maximum lamp current in a manner similar to that described above for a single atomic element hollow cathode lamp.

Referring now to FIG. 4, there is shown an atomic absorption spectrophotometer holding four single atomic element hollow cathode lamp assemblies HCL1 to HCL4 each in accordance with the lamp assembly HCL described above with reference to FIGS. 1 and 2 and each connected to measurement circuit means MCM and a microprocessor μP essentially as described above with reference to FIG. 3. The four lamp assemblies HCL1 to HCL4 are held in a turret TU operated by turret control means TUC to position a selected one of the four lamp assemblies HCL1 to HCL4 at a time in the optical path of the spectrophotometer. FIG. 4 shows the lamp assembly HCL1 in the optical path. Radiation emitted by the lamp assembly HCL1 passes from the respective cathode CA1 through an atomizer AT of the conventional flame type. Samples to be analysed by the spectrophotometer are fed into the atomizer AT from an automatic sampler AS operated by automatic sampler control means ASC and the atomizer is operated by atomizer control means ATC. Having passed through the atomizer AT, the radiation passes through a monochromator MN. The wavelength of the radiation passed by the monochromator MN is selected by wavelength control means MWC and the bandpass, that is to say the slit width, of the monochromator MN is selected by slit control means MSC. A photomultiplier tube detector DET provides an electrical current signal whose amplitude is proportional to the intensity of radiation emerging from the monochromator MN, and a logarithmic converter LG provides an amplified voltage signal proportional to the logarithm of the output of the detector DET. The concentration of the atomic element in respect of which the samples presented to the atomizer AT are analysed is essentially proportional to the output signal of the logarithmic converter LG.

The two electrodes of each of the lamp assemblies HCL1 to HCL4 are connected to the lamp power supply means LPS with only the hollow cathode electrodes CA1 etc being schematically shown in FIG. 4 with a single connection in each case. The resistor networks RN1 to RN4 of the respective lamp assemblies HCL1 to HCL4, each network having four respective resistors R1 to R4 as shown in FIGS. 1 and 3, are connected to a multiplexer MPX1. For simplicity of illustration only one connection is shown from each of the networks RN1 to RN4 to the multiplexer MPX1 although there is an individual connection from each of the sixteen resistors therein to the multiplexer MPX1. Each of these sixteen network resistors is connected in turn in series with the resistor R5 to the voltage source +V via the multiplexer MPX1 controlled by latch circuit means LH. The voltage across each of the sixteen network resistors is connected in turn to the analogue-to-digital converter ADC via a further multiplexer MPX2 which is also controlled by the latch circuit means LH. The multiplexers MPX1 and MPX2, the resistor R5, the voltage source +V, the latch circuit means LH and the analogue-to-digital converter ADC form the measurement circuit means MCM to which the networks RN1 and RN4 are connected. The output signal of the logarithmic converter LG is also connected to the analogue-to-digital converter ADC via the multiplexer MPX2. In operation of the spectrophotometer the networks RN1 to RN4 are measured by the measurement circuit means MCM as soon as the lamp assemblies HCL1 to HCL4 are connected thereto. Thereafter this measurement is repeated as a background check routine which is interrupted when it is necessary for another analogue signal produced by the spectrophotometer, for example the output of the logarithmic converter LG, to be applied to the analogue-to-digital converter ADC via the multiplexer MPX2. The background check routine can be used, for example, to provide an error signal if a lamp is not present in a required position.

A microcomputer MCP includes the microprocessor $\mu P$, a volatile read-write memory RAM for temporarily holding data for processing by the microprocessor $\mu P$, and a read-only memory ROM holding program information for conditioning the operation of the microprocessor $\mu P$. The bus BS connects the microprocessor $\mu P$ to the read-write memory RAM, to the read-only memory ROM, to the analogue-to-digital converter ADC, to the latch circuit means LH, to the lamp power supply LPS, to the turret control means TUC, to the automatic sampler control means ASC, to the atomizer control means ATC, to the slit control means MSC and to the wavelength control means MWC.

In addition to holding program information the read-only memory ROM also holds atomic element related information, including in particular wavelength information, at a location therein associated with the respective atomic element of each of a plurality of single atomic element hollow cathode lamp assemblies with which the spectrophotometer may be used. There may be in excess of sixty such single atomic element hollow cathode lamp assemblies but at any one time only one or some of these lamp assemblies, for example the four lamp assemblies HCL1 to HCL4, will be located in the spectrophotometer with their networks connected to the measurement circuit means MCM. The microprocessor $\mu P$ is conditioned to identify the atomic element of the one or some lamp assemblies whose networks are connected to the measurement circuit means MCM responsive to measurement of the respective network thereby. In the case of the four lamp assemblies HCL1 to HCL4 shown in FIG. 4 this identification is responsive to the output of the analogue-to-digital converter ADC in respect of the voltages measured successively across the resistors R1 and R2 of the respective networks RN1 to RN4 of the lamp assemblies. The microprocessor $\mu P$ is further conditioned to apply to the wavelength control means MWC wavelength information derived from the read-only memory ROM for that one of the one or some of lamp assemblies whose atomic elements are identified and the lamp of which furthermore is present in the optical path of the monochromator. The turret TU and turret control means TUC include means which enable the microprocessor $\mu P$ to identify the lamp present in the optical path of the monochromator.

The read-only memory ROM also holds lamp current information. The microprocessor $\mu P$ is conditioned to control the lamp power supply means LPS using this lamp current information for the one or some lamp assemblies whose atomic elements are identified via the measurement circuit means MCM. It is advantageous for the microprocessor $\mu P$ to use the maximum lamp current information derived from the networks RN1 to RN4 via the measurement circuit means MCM together with the lamp current information derived from the read-only memory ROM to control the lamp power supply means LPS. If the networks RN1 to RN4 did not contain the resistors R3 and R4 representative of the maximum lamp operating current of the respective lamp assemblies, then the lamp current information in the read-only memory ROM could be held at locations therein associated with the respective atomic element of each of the plurality of hollow cathode lamp assemblies with which the spectrophotometer may be used and could entirely define the operating current for the respective lamps.

For an analysis consisting of the operation of the spectrophotometer to analyse one or more samples in respect of the single atomic element of one of the plurality of hollow cathode lamp assemblies for which information is stored in the read-only memory ROM, both atomic element related information and sample related information are needed. Automatic operation of the spectrophotometer is facilated by both types of information being brought together to form an information set which is continuously stored for at least the duration of that analysis in a non-volatile read-write memory NVM. The microprocessor $\mu P$ is connected by the bus BS to the memory NVM and is conditioned to use that information set to control that analysis.

The atomic element related information for each information set in the memory NVM is derivable from the read-only memory ROM and transferred thereto by the microprocessor μP upon identification of the atomic element of the respective lamp assembly. This atomic element related information will include the wavelength information already mentioned together with slit width information for application to the slit control means MSC. The atomic element related information derivable from the read-only memory ROM will include information identifying fuel type and fuel rate for application to the atomizer control means ATC and may also include measurement time information. The time for which the output signal of the detector DET, received via the logarithmic converter LG, multiplexer MPX2 and analogue-to-digital converter ADC, is averaged by the microprocessor μP for noise reduction of that signal is determined by the measurement time.

The sample related information for each information set in the memory NVM may be entered into an appropriate location therein by the user of the spectrophotometer via a keypad KPD connected by the bus BS to the microprocessor μP. This sample related information will include the number of standard concentration samples to be held in the automatic sampler AS and information identifying the concentration of those standard samples. The feature of background correction, which is well known and therefore not otherwise mentioned in this specification, will normally be provided for use in the spectrophotometer and the sample related information will in this case also indicate whether or not background correction is to be used in a particular analysis. The atomic element related information may also include an overriding instruction to switch off background correction for atomic elements for which the wavelength of the radiadtion to be passed by the monochromator is above a certain value.

The results of an analysis of one or more samples in respect of a single atomic element are temporarily stored in the volatile read-write memory RAM of the microcomputer MCP and eventually outputted to a suitable recorder, for example a printer PRI shown connected by the bus BS to the microprocessor μP, and possibly also to a display (not shown).

It is convenient to mention here that the automatic sampler AS will be of a type specifically appropriate for use with a flame type atomizer AT. Furthermore the automatic sampler control means ASC will normally partly be specific to and located in the particular automatic sampler AS and partly be permanently associated with the microprocessor μP and located in the main body of the spectrophotometer. It is well known for atomic absorption spectrophotometers to be primarily provided with one type of atomizer and to be adaptable for use with the other type of atomizer as an accessory. For example it is known to have an atomic absorption spectrophotometer which is primarily for use in the flame mode but adaptable for use in the electrothermal mode; and in this case the atomizer control means ATC for the electrothermal furnace will normally be provided as an accessory with that furnace rather than being located in the main body of the instrument and permanently associated with the microprocessor μP. Appropriate sensors (not shown) will be provided so that the type of atomizer AT and automatic sampler AS are identified to the microprocessor μP for appropriate operation. In the case mentioned where the atomizer control means ATC is provided as an accessory part of the spectrophotometer, it can have its own non-volatile read-write memory to hold a plurality of sets of furnace heat cycle information, and this information which has been mentioned above as being derivable from the read-only memory ROM may instead remain in the non-volatile read-write memory of the electrothermal furnace atomizer control means ATC which may then be considered as part of the non-volatile read-write memory NVM holding the total information set for an analysis.

The non-volatile read-write memory NVM has the capacity to store a plurality of information sets as described above. Thus an analysis sequence consisting of the operation of the spectrophotometer to analyse one or more samples held in the automatic sampler AS in respect of each of a set of atomic elements in turn is controlled by the microprocessor μP being conditioned to use each of the plurality of information sets in turn, one information set for each atomic element of the set of elements. The plurality of information sets will be continuously stored in the read-write memory NVM for at least the duration of the analysis sequence. For example, the memory NVM will have the capacity to store at least four information sets, one for each of the four single atomic element hollow cathode lamp assemblies HCL1 to HCL4 shown in FIG. 4. With the use of four such lamp assemblies, the atomic element related information in each information set is derivable from the read-only memory ROM. The spectrophotometer may additionally be able to use lamps other than the lamp assemblies described with reference to FIGS. 1 to 5 which have networks identifying the respective atomic element. For example in each of the four turret lamp locations there may be accommodated a conventional single atomic element hollow cathode lamp. In this case the user of the spectrophotometer may simply provide, via the key pad KPD, information to the microprocessor μP identifying the atomic element of each lamp and in response thereto the microprocessor μP can derive all the necessary atomic element related information from the read-only memory ROM and transfer it for use into the non-volatile memory NVM. In a more precise reproduction of the function of any one of the resistor networks RN1 to RN4, the user could also provide information via the key pad KPD corresponding to the lamp current information of those networks. As another example, conventional electrodeless discharge lamps may be accommodated in each of the four turret lamp locations. In this case again the user will provide via the key pad KPD information identifying the respective atomic element of the lamp, and additionally the user will have to provide information for an auxiliary power supply for operating electrodeless discharge lamps. As another example, multiple atomic element hollow cathode lamps may be used. These lamps may be conventional, in which case the user will provide via the keypad KPD information identifying the lamp as a multiple element lamp, information identifying the atomic elements of the lamp and lamp current information. A possible modification is that the multiple atomic element hollow cathode lamp may be provided with a resistor network, to be measured by the measurement circuit means MCM, by which it will provide lamp current information and information identifying it as a multielement lamp. The user will then provide information via the keypad KPD identifying the atomic elements of the lamp and the microprocessor μP will be conditioned to derive atomic element related information from the read-only memory ROM and transfer it to a separate information set in the non-volatile read-write memory NVM for each of those atomic elements.

In addition to the ability to use lamps other than the lamp assemblies described with reference to FIGS. 1 to 3, the spectrophotometer may be provided with a manual override facility such that even when a lamp assembly having a network according to the invention is present the user will be able to enter, via the keypad KPD, atomic element related information into an information set in the non-volatile read-write memory NVM which is different to the information which would otherwise be derived from the read-only memory ROM.

An external computer (not shown) may be connected via a suitable interface circuit to the bus BS. One use of an external computer can be to further facilitate automatic operation of the spectrophotometer by augmenting the function of the non-volatile read-write memory NVM. For example once an information set consisting of atomic element related information and sample related information as described above has been entered into the non-volatile memory NVM for a particular analysis, that information set may be transferred to the external computer for recall at any later data for use in repetition of the same analysis even though the capacity of the non-volatile memory NVM may have been fully used for different analyses in the meantime.

It will be appreciated that in the above description of an atomic absorption spectrophotometer with respect to FIG. 4, only certain features of such a spectrophotometer have been mentioned and there are other features which conventionally are present or may be present. For example, the lamp power supply is normally modulated and the signal from the detector DET is correspondingly demodulated prior to processing by the logarithmic converter LG. Also the detector DET will be subject to gain control which may be automatic. Also double beam operation, that is the provision of a reference optical path which bypasses the atomiser and the use of the signal derived via this reference path to provide baseline correction which counteracts instrumental drift, particularly of the hollow cathode lamp output and the detector output, is a well known optional feature of atomic absorption spectrophotometers. In the case of the spectrophotometer described above with reference to FIG. 4 which is capable of automatic operation for a long period of time, double beam operation will be particularly advantageous and very likely incorporated.

Referring now to FIG. 5, there is shown a flow chart of an operation of the spectrophotometer shown in FIG. 4.

In operation 1 "Switch On" the user switches on the electrical supplies to the spectrophotometer. In operation 2 "Initialise", the user ensures that the four single atomic element hollow cathode lamp assemblies HCL1 to HCL4 are loaded by being located in the turret TU and electrically connected, and that four corresponding sample related information sets are located in the non-volatile read-write memory NVM. There will be only one loading position for the lamps which will coincide with the position in which a lamp is located on the optical axis of the spectrophotometer, that is to say the position of the lamp assembly HCL1 as shown in FIG. 4. As each lamp assembly is loaded in turn the microprocessor μP can transfer the relevant atomic element related information for the respective information set from the read-only memory ROM into an appropriate location in the non-volatile memory NVM responsive to measurement of the respective one of the lamp assembly networks RN1 to RN4 by the measurement circuit means MCM. At the time that each lamp is in the loading position the user can enter the relevant sample related information for the respective information set into the memory NVM via the key pad KPD and the microprocessor μP. It may be that the operation of the spectrophotometer is to be a repeat, for a new set of samples in the automatic sampler AS, of an immediately preceding analysis sequence for a different set of samples in respect of the atomic elements of the same lamp assemblies HCL1 to HCL4. If this is the case, the lamp assemblies will already be loaded and the corresponding information sets will be present in the non-volatile memory NVM prior to "Switch On" and the "Initialise" operation 2 will not need to be performed by the user. In operation 3 "Power to Lamps" the user switches on the lamp power supply means LPS to each lamp in turn and responsive to this action for each lamp in turn the appropriate lamp current information is derived from the non-volatile memory NVM by the microprocessor μP and applied to the lamp current supply means LPS. In the case where the atomiser AT is of the flame type an operation (not shown) after either operation 2 or 3 and involving action by the user is required to ignite the flame of the atomiser AT. In operation 4 "Start Automatic Sampler" the user initalises the operation of the automatic sampler AS, and responsive to this operation appropriate information is entered from the automatic sampler control means ASC into the read-write memory RAM after which the operation of the spectrophotometer can be entirely automatic under control of the microprocessor μP without further intervention by the user.

Responsive to operation 4, the microprocessor μP performs operation 5 "Set N=1". N represents a turret count. The turret count N determines which one of the four lamp assemblies HCL1 to HCL4 should be in the optical path for the duration of a run of the automatic sampler AS, that is to say an analysis of the samples therein for one atomic element, and it also determines which information set in the non-volatile memory NVM will be used by the microprocessor μP during that analysis. The turret count N is held in the read-write memory RAM for the duration of each analysis. Responsive to operation 5, the microprocessor μP performs operation 6 "Set Lamp Turret to N". In this operation the turret TU is driven to position N (At this page N=1 corresponding to say the lamp assembly HCL1) by the turret control means TUC. Responsive to operation 6, the microprocessor μP controls operation 7 "Set Slits" in which the monochromator MN slit width is set by the slit control means MSC using slit width information from the information set in the non-volatile memory NVM, and then the microprocessor μP controls operation 8 "Set Wavelength" in which the monochromator MN wavelength is set by the wavelength control means MWC using wavelength information from the information set in the non-volatile memory NVM. The gain of the detector DET will be automatically adjusted in conjunction with setting the monochromator wavelength. Also responsive to operation 6 the microprocessor μP will transfer measurement time information from the non-volatile memory NVM to the volatile read-write memory RAM for use by the microprocessor μP during subsequent measurements of the samples for the one atomic element.

Following operation 8, the microprocessor μP controls operation 9 "Measure Blank". In this operation, under control of the automatic sample control means ASC, the automatic sampler AS provides a sample to the atomizer AT having nominally zero concentration of the one atomic element for which the set of samples are to be analysed. This sample is atomized by the atomizer AT under control of the atomizer control means ATC, and the output signal of the detector DET is passed via the logarithmic converter LG and the multiplexer MPX2 and analogue-to-digital converter ADC of the measurement circuit means MCM to the microprocessor μP and the result is stored in the read-write memory RAM as a baseline measurement representing zero concentration of the atomic element for the duration of the analysis of the set of samples for that atomic element. In the case where the atomizer AT is of the flame type, the microprocessor μP will apply fuel type and fuel rate information from the non-volatile memory NVM to the atomizer control means ATC for the atomization of this and all subsequent samples in the analysis for the particular atomic element. Following operation 9, the microprocessor μP controls operation 10 "Measure Standards". In this operation, a predetermined number of standards, i.e. known concentration samples, which number is present in the relevant information set in the non-volatile memory NVM, are provided in turn by the automatic sampler AS to the atomizer AT. In each case the detector DET output signal is fed via the measurement circuit means MCM to the microprocessor μP and an absorbance result is calculated by comparison with the baseline measurement in the read-write memory RAM and then stored in the read-write memory RAM. Following operation 10, the microprocessor μP performs operation 11 "Calibrate". In this operation the microprocessor μP derives the known concentration values of the standard samples from the relevant information set in the non-volatile memory NVM and uses these concentration values together with the absorbance results for the standard samples, which have been stored in the read-write memory RAM in operation 10, to calculate a set of calibration coefficients which are then stored in the read-write memory RAM for the duration of the analysis for the one atomic element. These calibration coefficients enable the functions conventionally known as scale expansion and curvature correction to be applied to subsequent sample measurements.

Following operation 11, the microprocessor μP controls operation 12 "Measure Sample, Calculate and Store Concentration". In this operation, a sample from the set of samples which is to be analysed in respect of the single atomic element is provided by the automatic sample AS to the atomizer AT. The absorbance result for that sample derived from the output signal of the detector DET is applied to the read-write memory RAM, the calibration coefficients in the read-write memory RAM are applied to the absorbance result to produce a concentration result, and the concentration result is stored in the read-write memory RAM. Following operation 12, the microprocessor μP controls operation 13 "Automatic Sampler End?". In this operation the automatic sampler control means ASC senses whether or not the automatic sampler AS has reached the end of its run and does not have a further sample to be measured. If the answer is "No", operation 12 is repeated for the next sample. When operation 12 has been performed for all the samples and their respective concentration results stored in the read-write memory RAM, the next operation 13 will produce the answer "Yes" and the microprocessor μP will proceed to operation 14 "N=Limit?". In this operation the turret count N is checked to determine whether or not it corresponds to the number of turret positions, for example four turret positions as shown in FIG. 4. For the first analysis N=1 as set by operation 5, and so operation 14 produces the answer "No" in response to which the microprocessor μP performs operation 15 "$N=N+1$" in which it increments the value of the turret count N. Responsive to operation 15, the microprocessor μP performs operation 6 in which the turret TU is driven to the next position to bring the next lamp assembly HCL2 into the optical path of the spectrophotometer and operations 7 to 13 are repeated to provide another set of concentration results in the read-write memory RAM for the same set of samples in the autosampler AS in respect to the single atomic element of the next lamp assembly HCL2. When eventually operation 14 produces the answer "Yes" the microprocessor μP performs operation 16 "Print Formated Results and Stop". In this operation the concentration results of all the samples of the set of samples in the automatic sampler AS in respect of the atomic elements of all the single atomic element lamp assemblies HCL1 to HCL4 in the turret TU are extracted from the read-write memory RAM in formated form and printed by the printer PRI and the spectrophotometer is then stopped, that is to say most of the electrical supplies are switched off and a dormant condition is set. An analysis sequence for a new set of samples will then require the user to start the whole sequence of operations from operation 1.

Up to this point the spectrophotometer described is substantially the same as that described in the specification filed with our copending U.K. Patent Application No. 8133968 (PHB 32832) corresponding to U.S. patent application Ser. No. 436,205 now abandoned.

FIGS. 6A and 6B are flow charts which shows a sub-routine which is inserted between points A and C in the flow chart shown in FIG. 5, i.e. between operations 8 and 10. It should be noted that operation 9, i.e. measurement of the blank or the sample having nominally zero concentration of the element being analysed, is included in the subroutine shown in FIGS. 6A and 6B.

The sub-routine illustrated in FIGS. 6A and 6B enables the spectrophotometer to automatically set the optimum values for bandwidth of the monochromator, the gas flow to the burner and the intensity of the radiation source.

The procedure is as follows. Until operation 8 the procedure is idential to that described with reference to FIG. 5. A sub-routine 17, optimization is then entered having a first operation 18 to set a value for the gas flow to the burner. This is achieved by applying fuel type and fuel flow rate information under the control of the microprocessor μP from the non-volatile memory NVM to the atomizer control means ATC. Information as to the fuel type and flow rate is stored in the non-volatile memory NVM for each element to be detected and may be selected by means of the coded lamps or the keyed information as described in the slits, wavelength and lamp current.

Following operation 18 an optimization standard is aspirated into the flame from the automatic sampler AS under the control of the automatic sampler control means ASC operation 19.

The output signal of the detector DET is passed via the logarithmic converter LG and the multiplexer MPX2 and the analogue to digital converter ADC of the measurement circuit means MCM to the microprocessor $\mu P$ and the result is stored in the read-write memory RAM as an absorbance value. This is shown as operations 20 and 21 on the flow chart of FIG. 6A.

The microprocessor $\mu P$ then sends an instruction over the bus BS to the atomizer control means ATC to increase the fuel gas flow rate to the burner by one increment, operation 22. A new value of absorption is then measured, operation 23, by following the same procedure as described with reference to operations 19 and 20. The microprocessor $\mu P$ compares the new absorption value with the stored value, operation 24. If the new value is greater than the stored value the new value is stored in the read-write memory RAM, operation 26. The microprocessor $\mu P$ then outputs an instruction to the atomizer control means ATC to increase the fuel gas flow and operations 22 to 25 are repeated.

When, on repeating operation 25, the new absorbance value is less than the stored value the fuel gas flow rate is one increment greater than that which gives the maximum absorbance value for the optimization standard. The microprocessor $\mu P$ then issues an instruction to the atomizer control means ATC to decrease the fuel flow rate by one increment, operation 27. In order to reduce the effects of noise this procedure may be slightly modified by requiring two successive new absorbance values to be less than the stored value before deciding that a maximum value has been detected. This may be achieved either by repeating operations 22 to 25, in which case the fuel gas flow should be decreased by two increments if a true maximum is found or by repeating only operations 23 to 25. If the absorbance keeps increasing as the gas flow rate is increased up the maximum flow rate available the maximum flow rate is used. During the gas flow optimization background correction should be applied to reduce errors caused by absorption by the flame particularly at wavelengths less than 420 nanometers.

For certain elements there is little change in sensitivity with changing gas flows. For these elements the link shown in FIG. 6A from operation 21 direct to operation 28 is used. The microprocessor $\mu P$ will recognise these elements from the insertion of the hollow cathode lamp or from the keyboard inputs made by the operator.

Having optimised the fuel gas flow the microprocessor $\mu P$ controls operation 28 'Measure Blank'. In this operation, under the control of the automatic sampler control means ASC, the automatic sampler AS provides a sample to the atomizer AT having a nominal zero concentration of the one atomic element for which the set of samples is to be analysed. This sample is atomized by the atomizer AT under the control of the atomizer control means ATC, and the output signal of the detector DET is passed via the logarithmic converter LG, the multiplexer MPX2 and analogue to digital converter ADC of the measurement circuit means MCM to the microprocessor $\mu P$ and the result is stored in the read-write memory RAM as a baseline measurment representing zero concentration of the atomic element for which the set of samples is to be analysed.

The microprocessor $\mu P$ then uses the stored baseline measurement together with the stored absorbance value of the optimisation standard to calculate a true absorbance value for the optimisation standard, operation 29.

The microprocessor $\mu P$ then determines whether the true absorbance value of the optimisation standard is less than 0.5 absorbance units, operation 30, in FIG. 6B and if so then determines whether the absorbance of the optimization standard is greater than 0.1 absorbance units, operation 31.

If the true absorbance value of the optimization standard is between 0.1 and 0.5 absorbance units then the microprocessor $\mu P$ cause the lamp current, slit width, and selected wavelength set up in operations 3, 7 and 8 to be retained together with the optimized fuel gas flow operation 32 and the flow chart shown in FIG. 5 is re-entered at point C.

An absorbance unit A is equal to the $\log_{10} 1/T$ where T is the transittance and varies between 0 and 1. Total transmission or 100% transmittance being equal to 1 and zero transmission being equal to 0. Thus 50% transmittance will given an absorption of 0.3 A and 10% transmittance an absorption of 1.0 A.

If the true absorbance value of the optimization standard is less than 0.1 absorbance units this indicates that a sample having small concentrations of the element to be detected is being analysed. It is therefore necessary to obtain the maximum sensitivity from the instrument. A second set of parameters which is stored in the memory NVM and which give optimum conditions for trace analysis is selected by the microprocessor $\mu P$, operation 33, and applied to the lamp power supply LPS, and the slit control means MSC. In general these parameters will give a reduced lamp current and narrower slit width than the first set. As the lamp current is reduced the intensity of the radiation is reduced but the bandwidth of the radiation is also reduced. The reduced intensity can be tolerated at low absorbance levels as the signal reaching the detector DET will be correspondingly higher. Similarly the reduced slit width will reduce the energy passing through the monochromator but will increase the selectivity of the monochromator. The measurement time may also be modified, but whether this is increased or decreased will depend on the particular element to be detected. After having set the second set of parameters it may be necessary to re-optimize the fuel gas flow rate, operation 34, since when the slits are narrowed part of the flame is no longer in the optical path.

Since the instrument parameters have been altered it is necessary to re-measure the blank sample to reset the baseline, operation 35. When this operation has been completed the flow chart shown in FIG. 5 is re-entered at point C.

If the true absorbance value of the optimization standard is greater than 0.5 absorbance units the microprocessor $\mu P$ determines whether either an automatic diluter has been fitted or a manual dilution operation is to be carried out, operation 36. If no diluter has been fitted and no manual dilution is to be carried out the microporcessor $\mu P$ then determines whether the true absorbance value of the optimization standard is greater than 1.0 absorbance units, operation 37. If so the microprocessor $\mu P$ then determines whether an alternative wavelength is available, operation 38. Some hollow cathode lamps emit radiation at a plurality of discrete wavelengths and the corresponding element will absorb radiation at those discrete wavelengths.

If an alternative wavelength is available the microprocessor $\mu P$ controls operation 39 "set slits" in which the monochromator MN slit width is set by the slit control means using slit width information from an information set in the non-volatile memory NVM associated with the alternative wavelength for the particular element to be detected. The microprocessor μP then controls operation 40 'set wavelength' in which the monochromator MN wavelength is set by the wavelength control means MWC using the alternative wavelength information stored in the memory NVM.

The fuel gas flow rate to the burner is then re-optimized, operation 41, starting from a gas flow rate set by a value stored in the information set associated with the alternative wavelength and following the procedure shown in operations 18 to 29 of the sub-routine shown in FIG. 6.

At the end of operation 41 the microprocessor μP determines whether the true maximum absorbance value of the optimization standard is greater than 0.5 absorbance units, operation 42. After operation 42 the procedure re-enters the flow chart shown in FIG. 5 at point C. If the microprocessor μP determines an absorbance value greater than 0.5 absorbance units a warning indication is given to the operator, operation 43, but the analysis proceeds in the same manner as occurs when the absorbance value is less than 0.5 absorbance units i.e. using the same values for lamp current, wavelength, slit width and gas flow rate.

If, at operation 37, the microprocessor μP determines that the true absorbance value of the optimisation standard is less than 1.0 abosrbance units a third set of parameters which is stored in the memory NVM is selected by the microprocessor μP, operation 44, and applied to the lamp power supply LPS and the monochromator slit control means MSC. In general this will cause the lamp current to be increased to increase the intensity of the radiation emitted by the lamp and will cause the monochromator slit width to be increased to maximise the radiation passed along the optical path to the detector. These measures will decrease the selectivity of the analysis but this is less important with more highly concentrated samples.

It may be desirable to re-optimize the gas flow, operation 45, which will follow the same procedure described for operation 41, but frequently this step will be unnecessary and the flow chart shown in FIG. 5 may be re-entered at the point C directly from operation 44.

It at operation 38 the microprocessor μP determines that no alternative wavelength is available the procedure re-enters between operations 37 and 44 so that the third set of parameters is set.

If at operation 36 the microprocessor μP determines that an automatic diluter has been fitted or that manual dilution is to be carried out the optimization sample is diluted by a known factor and the absorbance value of the diluted sample re-measured, operation 46. The microprocessor μP then determines whether the absorbance of the diluted sample is less than 0.5 absorbance units, operation 47. If so then the next operation is operation 31 but if the absorbance is greater than 0.5 absorbance units the sample is further diluted and the procedure of operation 46 repeated. This procedure is repeated until the absorbance of the diluted sample is less than 0.5 absorbance units. the microprocessor μP will detect whether a diluter is fitted by means of electrical signals produced by fitting the diluter, for example the making of switch contacts and whether manual dilution is to be performed by means of an input from the keyboard KPD.

By providing three sets of parameters associated with each element to be detected in the memory NVM and selecting the set in accordance with the measured absorbance value of the optimisation standard it is possible to operate the spectrophotometer to maximum advantage without requiring the operator to optimise the operating conditions. If the coded hollow cathode lamps and automatic sampler are used the operator only has to ensure that the correct lamp is fitted and that the correct samples and standards are loaded into the sampler.

It is convenient to use a portion of the sample to be analysed as the optimization standard since the spectrophotometer will then be optimized for the particular analysis. However any sother convenient substance could be used but it is obviously preferable that the concentration of the optimization sample is similar to that of the sample to be analysed particularly in respect of the element to be detected.

In order to optimize the fuel gas flow it is necessary that the atomizer control means ATC can decode the microprocessor instructions and set the gas flow in incremental steps. The atomizer control means ATC includes a gas flow controller which, conveniently, responds to digital input signals. Such gas flow controllers are known in the art, an example being that described by T. W. Hunter and G. M. Hieftje in an article entitled 'Directly Digital Flow Controller with Rapid Response Time and High Precision' published in Analytical Chemistry, Volume 50, No. 2, February 1978, at pages 209 to 212 inclusive.

While it is convenient to use a spectrophotometer as described with reference to FIGS. 1 to 5 with the addition of the operations under the control of the microprocessor μP described with reference to FIGS. 6A and 6B to produce an embodiment of a spectrophotometer according to the invention it will be apparent to one skilled in the art that numerous modifications could be made while still using the invention which is defined by the claims. A larger or smaller number of sets of parameters may be stored and their selection may be made at different absorbance levels. The parameters to be set automatically may also include the measurement time which may be the same for each level of absorbance or may vary according to which set of parameters is selected. The microprocessor μP may cause the printer PRI to print out the set of parameters selected when automatic optimization has occurred. The absorbance values at which the various sets of parameters are selected have been found to be convenient for a particular instrument but may be altered if the design of the instrument is changed, for example when using a different type of monochromator or detector. The best absorbance value for selection of the various sets of parmaters can be found by experimentation.

The invention also relates to a method of atomic absorption spectrophotometry in which the operations carried out automatically in the spectrophotometer described hereinbefore with reference to FIGS. 1 to 6A and B are manually controlled by an operator using a non-automatic spectrophotometer.

In such a case the operator may set up the spectrophotometer to a first set of conditions dependent on the element to be detected. An optimization sample is then caused to be aspirated into the flame and the gas flow varied until the maximum absorbance is measured. The operator then selects sets of parameters according to maximum absorbance of the optimization standard and proceeds with the analysis using those parmeters. The sets of parameters may, for example, be derived from previous analysis, the settings for various levels of absorption having been noted and collated. It is, of course, more convenient if this process can be carried out automatically within the spectrophotometer using stored sets of parameters, but an operator could follow the same process using a commercially available spectrophotometer.

I claim:

1. An atomic absorption spectrophotometer comprising a flame atomizer,
   first means for setting parameters of the spectrophotometer to a first set of preset values dependent on a substance to be detected,
   second means for setting a fuel gas flow rate to a burner to a preset value dependent on said substance to be detected,
   third means for aspirating an optimization standard into a flame of said flame atomizer,
   fourth means for incrementally changing said gas flow rate and for measuring absorbance of said optimization standard at each incremental change of said gas flow rate, and
   fifth means for selecting one of a plurality of stored sets of parameters of said spectrophotometer depending on said absorbance of said optimization standard.

2. An atomic absorption spectrophotometer comprising a flame atomizer,
   first means for setting parameters of the spectrophotometer to a first set of preset values dependent on a substance to be detected,
   second means for setting a fuel gas flow rate to a burner to a preset value dependent on said substance to be detected,
   third means for aspirating an optimization standard into a flame of said flame atomizer,
   fourth means for measuring absorbance of said optimization standard, and
   fifth means for selecting one of a plurality of stored sets of parameters of said spectrophotometer depending on said absorbance of said optimization standard,
   wherein there is further included sixth means for storing measured absorbance values, seventh means for modifying said gas flow rate in incremental steps, wherein said fourth means measures said absorbance of said optimization standard at each of said incremental steps, and eighth means for comparing said measured absorbance at each of said steps with said measured absorbance at the preceding step to determine said flow rate providing a maximum one of said absorbance values; and wherein said fifth means operates in dependence on said maximum absorbance value.

3. An atomic absorption spectrophotometer according to claim 2, wherein a first set of parameters is retained if said maximum absorbance value or said absorbance of said optimization standard is in the range of 0.1 to 0.5 Absorbance Units; a second set of parameters is used if said maximum absorbance value or said absorbance of said optimization standard is less than 0.1 Absorbance Units; and a third set of parameters is used if said maximum absorbance value or said absorbance of said optimization standard is greater than 0.5 Absorbance Units.

4. An atomic absorption spectrophotometer according to claim 3, further comprising ninth means for selecting radiation of an alternative wavelength, wherein said maximum absorbance value or said optimization standard is greater than 1.0 Absorbance Units.

5. An atomic absorption spectrophotometer according to claim 4, further comprising tenth means for indicating said maximum absorbance value or said absorbance of said optimization standard, wherein said maximum absorbance value or said absorbance of said optimization standard is greater than 0.5 Absorbance Units.

6. An atomic absorption spectrophotometer according to claim 4, further comprising eleventh means for diluting said optimization standard, wherein said twelfth means is activated when said maximum absorbance value or said absorbance of said optimization standard is greater than 0.5 Absorbance Units, said twelfth means being effective to bring said maximum absorbance value or said absorbance of the diluted optimization standard within the range 0.1 to 0.5 Absorbance Units.

7. An atomic absorption spectrophotometer according to claim 2, further comprising ninth means for selecting radiation of an alternative wavelength, wherein said maximum absorbance value or said optimization standard is greater than 1.0 Absorbance Units.

8. An atomic absorption spectrophotometer according to claim 7, further comprising tenth means for indicating said maximum absorbance value or said absorbance of said optimization standard, wherein said maximum absorbance value or said absorbance of said optimization standard is greater than 0.5 Absorbance Units.

9. An atomic absorption spectrophotometer according to claim 8, further comprising eleventh means for diluting said optimization standard, wherein sid eleventh means is activated when said maximum absorbance value or said absorbance of said optimization standard is greater than 0.5 Absorbance Units, said twelfth means being effective to bring said maximum absorbance value or said absorbance of the diluted optimization standard within the range 0.1 to 0.5 Absorbance Units.

10. An atomic absorption spectrophotometer according to claim 2, further comprising tenth means for indicating said maximum absorbance value or said absorbance of said optimization standard, wherein said maximum absorbance value or said absorbance of said optimization standard is greater than 0.5 Absorbance Units.

11. An atomic absorption spectrophotometer according to claim 10, further comprising eleventh means for diluting said optimization standard, wherein said eleventh means is activated when said maximum absorbance value or said absorbance of said optimization standard is greater than 0.5 Absorbance Units, said twelfth means being effective to bring said maximum absorbance value or said absorbance of the diluted optimization standard within the range 0.1 to 0.5 Absorbance Units.

12. An atomic absorption spectrophotometer according to claim 2, further comprising eleventh means for diluting said optimization standard, wherein said eleventh means is activated when said maximum absorbance value or said absorbance of said optimization standard is greater than 0.5 Absorbance Units, said twelfth means being effective to bring said maximum absorbance value or said absorbance of the diluted optimization standard within the range 0.1 to 0.5 Absorbance Units.

13. An atomic absorption spectrophotometer according to claim 1, further comprising means for aspirating and measuring absorbance of said substance to be detected, wherein a selected set of parameters is used.

14. A method of analysis using an atomic absorption spectrophotometer including a flame atomizer comprising the steps of
   (a) setting parameters of the spectrophotometer to a set of preset values dependent on a substance to be detected,
   (b) setting a gas flow rate to a burner to a preset value dependent on said substance to be detected,
   (c) aspirating an optimization standard into a flame of said flame atomizer,
   (d) measuring absorbance of said optimization standard and storing the measured value,
   (e) modifying said gas flow rate in incremental steps,
   (f) measuring new absorbance values for each incremental step of flow rate,
   (g) comparing each newly measured absorbance value with the stored value until a maximum absorbance measurement value is found,
   (h) using said maximum absorbance measurement value to select one of a plurality of sets of parameters for said spectrophotometer, and
   (i) subsequently aspirating and measuring absorbance of a sample using said selected set of parameters.

15. A method according to claim 14, wherein a portion of said sample is used as said optimization standard.

16. A method according to claim 15, wherein a first set of parameters is selected if said absorbance value is less than 0.1 Absorbance Units, the original set of parameters is retained if said absorbance value is between 0.1 and 0.5 Absorbance Units, and a third set of parameters is selected if said absorbance value is greater than 0.5 Absorbance Units.

17. A method according to claim 16, wherein a further step of choosing an alternative wavelength is included if said maximum absorbance value is greater than 1.0 Absorbance Units, and said steps (b) through (g) are subsequently repeated.

18. A method according to claim 17, wherein a warning signal is produced if said absorbance value at the end of repeated steps (g) is greater than 0.5 Absorbance Units.

19. A method according to claim 15, wherein if said maximum absorbance value of said optimization standard is greater than a preset value, said optimization standard is diluted and absorbance is remeasured, and wherein this procedure is repeated until said maximum absorbance value becomes less than said preset value.

20. A method according to claim 19, wherein said preset value is 0.5 Absorbance Units.

21. A method according to claim 14, wherein a first set of parameters is selected if said absorbance value is less than 0.1 Absorbance Units, the original set of parameters is retained if said absorbance value is between 0.1 and 0.5 Absorbance Units, and a third set of parameters is selected if said absorbance value is greater than 0.5 Absorbance Units.

22. A method according to claim 14, wherein a further step of choosing an alternative wavelength is included if said maximum absorbance value is greater than 1.0 Absorbance Units, and said steps (b) through (g) are subsequently repeated.

23. A method according to claim 14, wherein a warning signal is produced if said absorbance value at the end of repeated steps (g) is greater than 0.5 Absorbance Units.

* * * * *

UNITED STATES PATENT AND TRADEMARK OFFICE
CERTIFICATE OF CORRECTION

PATENT NO. : 4,634,277

DATED : Jan. 6, 1987

INVENTOR(S) : Trevor J. Stockdale

It is certified that error appears in the above-identified patent and that said Letters Patent is hereby corrected as shown below:

Col. 1, line 57, change "cmparing" to --comparing--

Col. 16, line 14, change "sother" to --other--

Claim 6, Col. 18, line 13 change "twelfth" to --eleventh-- line 16, change "twelfth" to --eleventh--

Claim 9, Col. 18, line 33 change "sid" to --said--
line 36, change "twelfth" to --eleventh--

Claim 11, Col. 18, line 52, change "twelfth" to --eleventh--

Claim 12, Col. 18, line 61, change "twelfth" to --eleventh--

Signed and Sealed this

First Day of December, 1987

Attest:

DONALD J. QUIGG

*Attesting Officer*  *Commissioner of Patents and Trademarks*